United States Patent
Gilreath et al.

(10) Patent No.: US 8,185,185 B2
(45) Date of Patent: May 22, 2012

(54) SYSTEM AND METHOD FOR ASSESSING A PATIENT CONDITION USING TERTILES DERIVED FROM CAPSULE ENDOSCOPE IMAGES OF THE SMALL BOWEL

(75) Inventors: Mark G. Gilreath, Cumming, GA (US); Blair Lewis, NY, NY (US); Mordechai Frisch, Moreshet (IL); Deborah Mutter, Duluth, GA (US); Hagit Ephrath, Karkur (IL); Eddie Rudyk, Haifa (IL); Alan I. Klevens, Roswell, GA (US); Tal Davidson, Yoqneam Illit (IL)

(73) Assignee: Given Imaging Ltd., Yoqneam (IL)

( * ) Notice: Subject to any disclaimer, the term of this patent is extended or adjusted under 35 U.S.C. 154(b) by 1305 days.

(21) Appl. No.: 11/730,580

(22) Filed: Apr. 2, 2007

(65) Prior Publication Data
US 2007/0255095 A1 Nov. 1, 2007

Related U.S. Application Data

(60) Provisional application No. 60/787,696, filed on Mar. 31, 2006.

(51) Int. Cl.
*A61B 5/00* (2006.01)

(52) U.S. Cl. ........ 600/407; 600/117; 600/118; 600/424; 600/425

(58) Field of Classification Search .......... 600/109, 600/160, 300, 462, 473, 476–477, 407, 425, 600/117, 118, 424; 128/899, 920, 922; 348/65; 382/128
See application file for complete search history.

(56) References Cited

U.S. PATENT DOCUMENTS

| 4,278,077 A | 7/1981 | Mizumoto |
| 5,604,531 A | 2/1997 | Iddan et al. |
| 5,993,378 A | 11/1999 | Lemelson |
| 6,240,312 B1 | 5/2001 | Alfano et al. |
| 6,819,785 B1 | 11/2004 | Vining et al. |
| 7,009,634 B2 | 3/2006 | Iddan et al. |
| 7,039,453 B2 | 5/2006 | Mullick |
| 2002/0103417 A1 | 8/2002 | Gazdzinski |

(Continued)

FOREIGN PATENT DOCUMENTS

CN 1777390 A 5/2006

(Continued)

OTHER PUBLICATIONS

Kornbluth et al., Video Capsule Endoscopy in Inflammatory Bowel Disease Past, Present, and Future, Inflamm Bowel Dis., vol. 10, No. 3, May 2004.*

(Continued)

*Primary Examiner* — Brian Casler
*Assistant Examiner* — Rajeev Siripurapu
(74) *Attorney, Agent, or Firm* — Pearl Cohen Zedek Latzer, LLP (57) ABSTRACT

A system and method are disclosed, which combine image data of a patient, such as images of the patient's GI tract, with rating mucosal damage. According to some embodiments of the present invention the system and method are able to assess a patient's GI tract condition, to monitor mucosal healing in a patient's GI tract, preferably, the small bowel (SB) mucosa and/or to differentiate between different pathological conditions. The system and method of the invention can provide a value or score arrived at by assigning a grade relating to one or more predetermined parameters.

12 Claims, 5 Drawing Sheets

U.S. PATENT DOCUMENTS

| | | | |
|---|---|---|---|
| 2002/0171669 A1 | 11/2002 | Meron et al. | |
| 2002/0177779 A1 | 11/2002 | Adler et al. | |
| 2003/0167000 A1* | 9/2003 | Mullick et al. | 600/424 |
| 2004/0225223 A1* | 11/2004 | Honda et al. | 600/476 |
| 2005/0074151 A1 | 4/2005 | Chen | |
| 2006/0069317 A1* | 3/2006 | Horn et al. | 600/300 |

FOREIGN PATENT DOCUMENTS

| | | |
|---|---|---|
| DE | 344 0177 | 5/1986 |
| JP | 57-45833 | 3/1982 |
| JP | 4-109927 | 4/1992 |
| JP | 1992-144533 | 5/1992 |
| JP | 2003-506797 | 2/2003 |
| JP | 2004-521693 | 7/2004 |
| JP | 2004-337596 | 12/2004 |
| WO | WO 2005/057498 | 6/2005 |
| WO | WO 2005/062715 | 7/2005 |
| WO | WO 2007029819 A1 | 3/2007 |

OTHER PUBLICATIONS

Clamp, S., Diagnosis of inflammatory bowel disease: an international multicentre scoring system, British Medical Journal, vol. 284 (Jan. 1982).*

Office Action issued in Chinese Patent Application No. 200710101644.X and dated Feb. 28, 2011.

Das et al., "Prediction of outcome of acute GI hemorrhage: a review of risk scores and predictive models", Gastrointestinal Endoscopy 60: 85-93, Jul. 1, 2004.

European Search Report issued for European Application No. 07 10 5441 and dated Sep. 1, 2011.

U.S. Appl. No. 13/051,229, filed Mar. 18, 2011, Boskovitz et al.

Office Action issued for Japanese Patent Application No. 2007-096552, dated Jan. 4, 2012.

* cited by examiner

| | | NORMAL | EDEMATOUS | EDEMATOUS WHITE TIPPED |
|---|---|---|---|---|
| VILLOUS APPEARANCE 510 | NUMBER | | | |
| | LONGITUDINAL EXTENT | SHORT SEGMENT | LONG SEGMENT | WHOLE REGION |
| | DISTRIBUTION PATTERN | LOCALIZED | PATCHY | DIFFUSE |
| DENUDED MUCOSA 520 | NUMBER | NONE | SINGLE | FEW |
| | LONGITUDINAL EXTENT | SHORT SEGMENT | LONG SEGMENT | WHOLE REGION |
| | DISTRIBUTION PATTERN | LOCALIZED | PATCHY | DIFFUSE |
| ULCER 530 | 532 NUMBER | NONE | SINGLE | FEW |
| | 534 LONGITUDINAL EXTENT | SHORT SEGMENT | LONG SEGMENT | WHOLE REGION |
| | 536 DISTRIBUTION PATTERN | LOCALIZED | PATCHY | DIFFUSE |
| | 538 SHAPE | CIRCULAR | LINEAR 533 | IRREGULAR |
| | 539 SIZE | <1/4 | 1/4-1/2 | >1/2 |
| Stenosis 540 | NUMBER | NONE | SINGLE | MULTIPLE |
| | LONGITUDINAL EXTENT | NON ULCERATED | ULCERATED | |
| | DISTRIBUTION PATTERN | TRAVERSED | NOT TRAVERSED | |

FIG.5

SYSTEM AND METHOD FOR ASSESSING A PATIENT CONDITION USING TERTILES DERIVED FROM CAPSULE ENDOSCOPE IMAGES OF THE SMALL BOWEL

CROSS REFERENCE TO RELATED APPLICATIONS

This application claims the benefit of U.S. Provisional Application, Ser. No. 60/787,696, filed on Mar. 31, 2006 which is incorporated in its entirety herein by reference.

FIELD OF THE INVENTION

The present invention relates to a system and method for assessing a patient condition. More specifically, the present invention relates to a system and method for assessing inflammatory or mucosal changes in a patient's GI tract.

BACKGROUND OF THE INVENTION

It's estimated that up to 1 million Americans suffer from inflammatory bowel disease. Inflammation of the bowel typically causes changes in the mucosa or the gastrointestinal (GI) tract wall tissue. Inflammatory bowel disease typically refers to two chronic diseases that cause inflammation of the intestines: ulcerative colitis and Crohn's disease. The most common symptoms of both ulcerative colitis and Crohn's disease are diarrhea and abdominal pain.

Inflammatory bowel disease can be hard to diagnose because there may be no symptoms, even if the person's bowel has become increasingly damaged for years. Once symptoms do appear, they often resemble those of other conditions, which may make it difficult for doctors to diagnose.

To date, inflammatory bowel disease is monitored by physicians noting a patient's symptoms and manually giving a score based on the reported symptoms. However, there is not always a full correlation between the symptoms and the patient's real condition.

SUMMARY OF THE INVENTION

Embodiments of the present invention provide a system and method, which combine image data of a patient, such as images of the patient's GI tract, with rating mucosal damage.

According to some embodiments of the present invention there is provided a system and method to assess a patient's GI tract condition, to monitor mucosal healing in a patient's GI tract, preferably, the small bowel (SB) mucosa and/or to differentiate between different pathological conditions. The invention provides a value or score arrived at by assigning a grade relating to one or more predetermined parameters.

Further embodiments of the present invention provide a scoring index for small intestinal mucosal condition. According to one embodiment of the invention a score is derived by computation and use of an algorithm to grade one or more predetermined parameters. Typically, these parameters define mucosal damage to the GI tract tissue. These parameters may be assessed through viewing images of the GI tract. The images may be captured for example by an endoscope, a capsule endoscope, or other in-vivo imaging device.

The method according to embodiments of the invention may be performed routinely or as a follow-up on patients at risk (e.g., patients with Crohn's disease, patients after chemotherapy, patients taking NSAIDs). The method according to embodiments of the invention may also be used to monitor progression of a treatment. Other uses may be provided by embodiments of the invention.

According to one embodiment of the present invention, a series of images of the lumen being monitored (e.g. a section of the GI tract, such as the small bowel (SB) or colon) may be collected. For example, images of the GI tract may be collected by a swallowable imaging capsule and may be wirelessly transmitted to an external receiver/recorder. The images may then be downloaded to a workstation for further processing and for displaying to the user. The series of images (typically can also be shown as a movie) may be divided into several segments and the scoring may be performed for each segment or for a sub series of images from each segment.

According to another embodiment of the present invention, a movie of the SB or other portion of the GI tract may be divided into segments based on a time bar provided, for example with the movie, for example, a capsule endoscopy movie. A user may go through the segment or through a series of images from that segment and may select images to be used for scoring, for example by capturing images as thumbnails. Each thumbnail may be dragged or may otherwise be imported to a page in a reporting section of the capsule endoscopy viewing software (e.g., the RAPID™ software). The page may include buttons, which may be used for entering parameter values for several predetermined parameters. The user may enter a value (descriptive or numerical) for each parameter per image, by clicking the buttons and a software may assign a weight to the parameter values and compute a final score for the selected images. The final score may be presented to the user on the workstation monitor. The score may be used to assess the condition of a SB mucosal tissue. The score may be used to assess a patient's condition and/or to differentiate between different pathological conditions.

According to an embodiment of the invention there is provided a method to assess inflammatory changes in a patient's GI tract. The method includes the steps of: providing a series of images of the GI tract to a viewer; dividing the series of images into segments; receiving a score for at least one image from each segment, the score relating to at least one parameter defining mucosal damage; and combining the scores to obtain a final score. The series of images may be images of the small bowel. According to one embodiment the step of dividing the series of images includes diving the series of images into three segments. According to one embodiment the segments are equally long segments.

The parameter defining mucosal damage can be: villus appearance; denuded mucosa; ulceration; and stenosis or a combination of all or some thereof.

According to one embodiment the method includes receiving a value for one or more factor selected from the group consisting of number, longitudinal extent, distribution pattern, shape, size and traverse.

The method may include creating a thumbnail of at least one image. The method may include creating a report which includes the thumbnail and the final score.

The method may include displaying the final score.

According to some embodiments of the invention there is provided a system for assessing a patient's GI tract mucosa. The system may include a display to display at least one image of the patient's GI tract; and a processor to accept a score for the image and to calculate a final score based on the score for the image, wherein said score for the image comprises a value of a parameter defining mucosal condition. The display may also include a time bar to show a time elapsed for the image.

According to one embodiment the system includes a processor to divide a stream of images of the patient's GI tract into a plurality of segments. The segments may be of an equal length. According to some embodiments the system may include a processor to generate a report, said report comprising a combination of scores for the image. The report may also include a thumbnail of the image.

According to some embodiments the parameter defining mucosal condition can include villus appearance; denuded mucosa; ulceration; and stenosis. According to some embodiments the system includes a swallowable capsule having an imaging device; and a receiver to receive image data from the swallowable capsule.

According to a further embodiment of the invention there is provided a method for determining the condition of a small bowel, the method including the steps of: providing a plurality of images of the small bowel; identifying mucosal damage in the images, thereby identifying damage containing images; and determining an extent of the damage based on a fraction of damage containing images from the plurality of images. The mucosal damage may be a lesion (for example, an ulceration) and the extent may be size. The extent may include also shape or other factors.

According to one embodiment determining a final score is based on the extent of the damage.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general-purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general-purpose systems may be used with programs in accordance with the teachings herein, or it may prove convenient to construct a more specialized apparatus to perform the desired method. It will be appreciated that a variety of programming languages may be used to implement the teachings of the invention as described herein.

Figure 1:
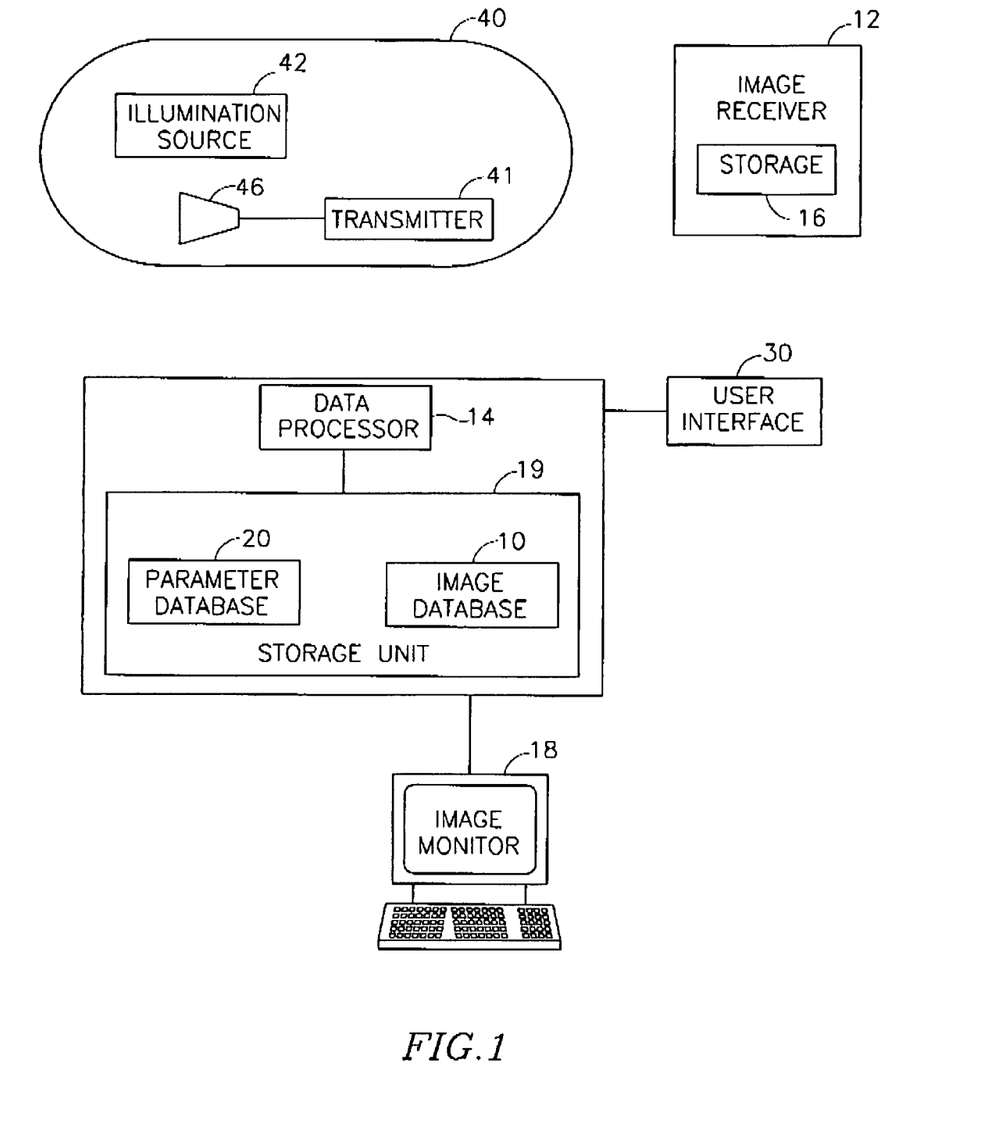
FIG. 1 shows a schematic diagram of an imaging system according to one embodiment of the present invention.

Reference is made to FIG. 1, which shows a schematic diagram of an imaging system according to one embodiment of the present invention. In an exemplary embodiment, the system may include an in vivo device 40, for example a capsule or other suitable device, having an imager 46, for capturing images, an illumination source 42, for illuminating the body lumen, and a transmitter 41, for transmitting and/or receiving data such as images and possibly other information to or from a receiving device. In alternate embodiments device 40 may be other than a capsule; for example, device 40 may be an endoscope, or other in vivo imaging device. An optical system, including, for example, a lens or plurality of lenses, may aid in focusing reflected light onto the imager 46. The device 40 may be inserted into a patient by for example swallowing and preferably traverses the patient's GI tract. In certain embodiments, the device and image capture system may be similar to embodiments described in U.S. Pat. No. 5,604,531 or in U.S. Pat. No. 7,009,634 to Iddan et al., issued Mar. 7, 2006 both assigned to the common assignee of the present application and incorporated by reference herein. In alternate embodiments, other image capture devices, having other configurations, and other image capture systems, having other configurations, may be used.

Preferably, located outside the patient's body in one or more locations, are an image receiver 12, preferably including an antenna or antenna array, an image receiver storage unit 16, a data processor 14, a data processor storage unit 19, and an image monitor 18, for displaying, inter alia, the images recorded by the device 40 and other information. Preferably, the image receiver 12 and image receiver storage unit 16 are small and portable, and are worn on the patient's body during recording of the images. Data processor storage unit 19 may include an image database 10 and a parameters database 20 e.g. a pathology parameters, scoring or other database, which may include for example data such as Capsule Endoscopy Standard Terminology (CEST), which may be used for preparing a report e.g. a scoring report, for assessing a patient condition. Preferably, data processor 14, data processor storage unit 19 and monitor 18 are part of a personal computer or workstation which may include components such as processor 14, a memory, a disk drive, and input-output devices, although alternate configurations are possible, and the system and method of the present invention may be implemented on various suitable computing systems. Database 20 may be in other locations, and may store information other than pathologies or CEST, for example, database 20 may be remote or accessed via a network such as the Internet.

Data processor 14 may include any suitable data processor, such as a microprocessor, multiprocessor, accelerator board, or any other serial or parallel high performance data processor. Image monitor 18 may be a computer screen, a conventional video display, or any other device capable of providing image or other data.

Preferably, the imager 46 is a suitable CMOS camera such as a "camera on a chip" type CMOS imager. In alternate embodiments, the imager 46 may be another device, for example, a CCD. According to some embodiments a 320× 320 pixel imager may be used. Pixel size may be between 5 to 6 micron. According to some embodiments pixels may be each fitted with a micro lens. The illumination source 42 may be, for example, one or more light emitting diodes, or another suitable light source.

In operation, imager 46 may capture images and may send data representing the images to transmitter 41, which may transmit images to image receiver 12 using, for example, electromagnetic radio waves. Image receiver 12 may transfer the image data to image receiver storage unit 16. After a certain time of data collection, the image data stored in storage unit 16 may be sent to the data processor 14 or the data processor storage unit 19. For example, the image receiver storage unit 16 may be taken off the patient's body and connected to a personal computer or workstation which includes the data processor 14 and data processor storage unit 19 via a standard data link, e.g., a serial or parallel interface of known construction. The image data may be then transferred from the image receiver storage unit 16 to the image database 10 within data processor storage unit 19. Data processor 14 may analyze the data and provide the analyzed data to the image monitor 18, where a health professional may view the image data. Data processor 14 may operate software which, in conjunction with operating software such as an operating system and device drivers, may control the operation of data processor 14. Preferably, the software controlling data processor 14 includes code written in the C++ language and possibly additional languages, but may be implemented in a variety of known methods. In other embodiments intermediate receiver 12 need not be used.

The database 20 which may be included in storage unit 19 may be contained within for example a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storage. A pathology database may contain for example CEST and/or, known pathologies or cases, known diseases, tumors and specific tissues. Known pathologies may include polyps, lesions, bleeding etc. The database 20 may also contain other information related to each image, for example, scoring results, scoring formulas, text information, keywords, descriptions, a complete medical diagnosis, relevant cases, articles or images, for example, images of the close areas, images of pathology or any other information. In other embodiments, other reference data, such as a list of parameters related to mucosal damage, may be contained within database 20 for the purpose of scoring analyzing and preparing a diagnostic report based on the images captured by the imaging device 40.

The image data collected and stored may be stored indefinitely, transferred to other locations, manipulated or analyzed. A health professional may grade several predetermined parameters of GI tract, e.g. the SB, for one or more images. The system may provide information such as a final score, which may indicate the condition of the mucosal tissue displayed in the images. According to some embodiments the system may provide information on the mucosal tissue of the patient and/or of the patient's medical condition. While, using a system where the data processor storage unit 19 first collects data and then transfers data to the data processor 14, the image data is not viewed in real time, other configurations allow for real time viewing.

The image monitor 18 may present the image data, preferably in the form of still and moving pictures, and in addition may present other information. In an exemplary embodiment, such additional information may include, but is not limited to a time line to show the time elapsed for each image, images in which pathology, such as bleeding, had been identified, the location of the swallowable capsule in the patient's abdomen, etc. In an exemplary embodiment, the various categories of information are displayed in windows. Multiple monitors may be used to display image and other data.

Preferably, the in vivo imaging system collects a series of still images as it traverses the GI tract. The images may be later presented as, for example, a stream of images or a movie of the traverse of the GI tract. The in vivo imager system may collect a large volume of data, as the in vivo device 40 may take several hours to traverse the GI tract, and may record images at a rate of, for example, two images every second, resulting in the recordation of thousands of images. The image recordation rate (or frame capture rate) may be varied.

Figure 2:
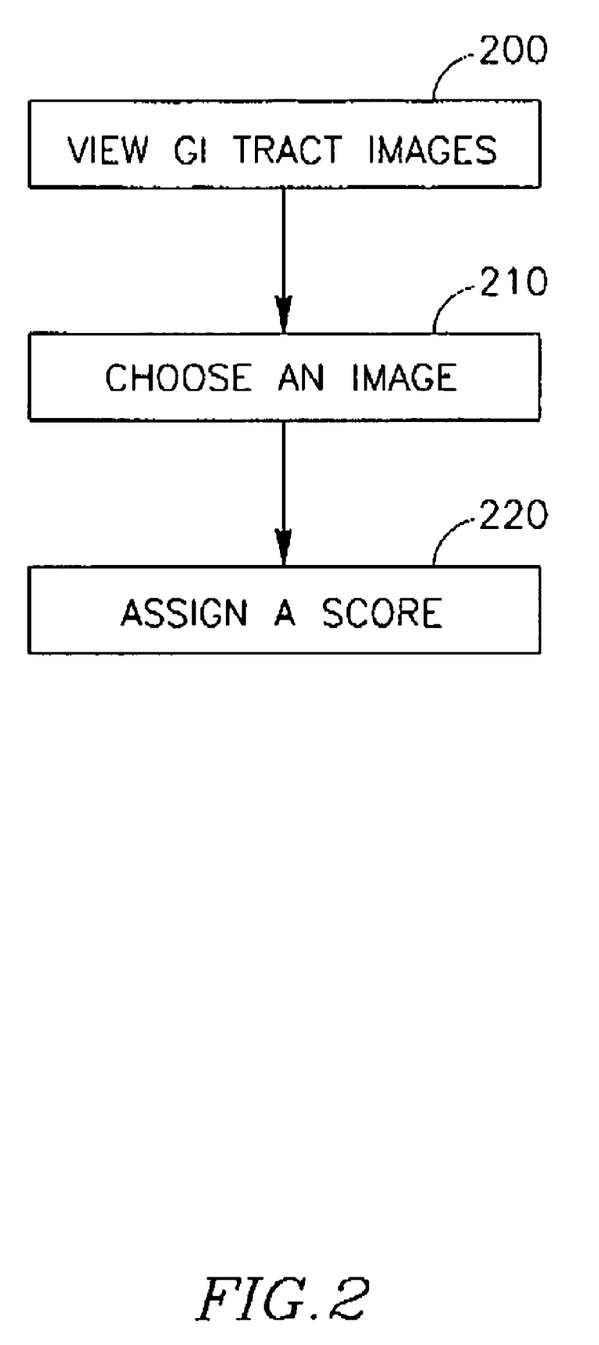
FIG. 2 depicts a flowchart of a method to assess a patient's GI tract condition, according to one embodiment of the present invention.

Reference is now made to FIG. 2, which depicts a flowchart of a method to assess a patient's GI tract condition, according to one embodiment of the present invention. In step 200 a user may view a series of images, for example, GI tract images received for example, from an endoscope, or from an in vivo imaging device such as device 40. The images may be stored in a dedicated database or may be viewed in real time while being transferred, for example from an in vivo device located inside a patient's body. The user may view the images on a monitor, which may be a part of a personal computer, a workstation, PDA etc. In step 210, the user may choose or select one or more images of interest or a portion of an image from the series of images. A series of images may be divided into portions based on anatomical regions displayed by the images. Choosing may be done by operating a user interface, such as a keyboard, a joystick a mouse or any other input device. The image chosen by the user may be displayed on a special display screen. In step 220, the user may assign a descriptive or numerical value to an image, value relating to one or several predetermined parameters. In one embodiment, a user may assign a mark or grade to several predetermined parameters that he may select from the database 20.

In one embodiment, a user may send a command via for example user interface 30, which may be, for example, a keyboard, a joystick, a mouse or any other suitable input-output device to data processor 14 in data processor storage unit 19. Data processor 14 may operate any suitable scoring calculation or calculation software or process to determine a final score based on several parameter marks or grades assigned by the user. The software, algorithm or processes used for scoring may be based on a numerical, logical or semantic computation involving parameter values, predetermined database constants and weights, terms and formulas.

The process of reporting, classifying and scoring may be performed in different modes, for example, in an automatic mode, in which the system searches the image database 10 for a match to pathology and may automatically calculate a medical score or a classification result for the patient. In a semi-automatic mode a health professional may, for example, enter, mark or fill an analysis table e.g. a scoring report, for an image or part of an image or a number of images and then as output may receive a diagnosis, classification or a scoring result for the selected frame(s), which would typically include a sum, according to one embodiment—a weighted sum, or other combination of the grades given to each image. In a manual mode, a health professional may enter a value for one or more predefined parameters as viewed in an image or a number of images and may request a scoring result based on the values entered. In one embodiment of the invention, a health professional may get confirmation of a diagnosis or a scoring report for better understanding of the patient situation. Other modes or methods for matching may be used.

The scoring results may be displayed using various suitable methods, for example, a list of results ordered according to image correlation, display of a final scoring correlated to the selected images in the captured image stream or any other suitable method. The scoring results may include for example a score displayed graphically as a bar, a ruler, a numerical value or any other way.

Figure 3:
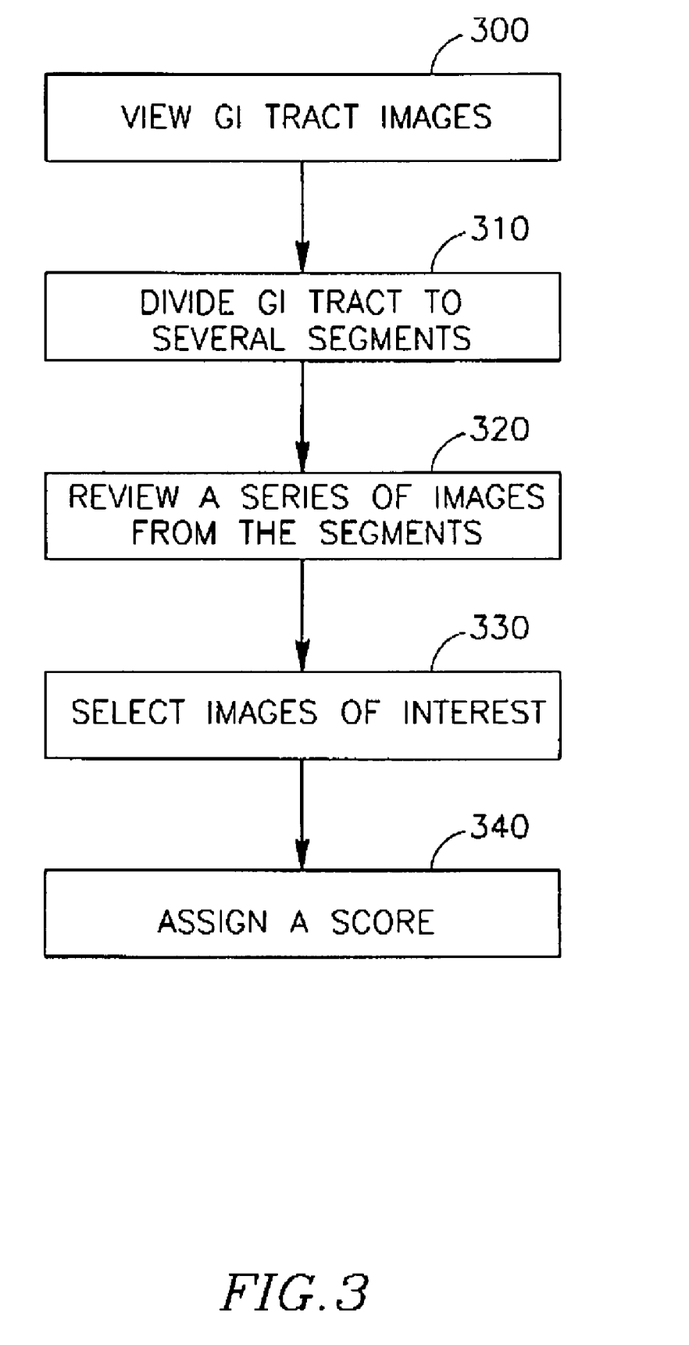
FIG. 3 depicts a flowchart of a method to assess inflammatory changes in a mucosal tissue, according to one embodiment of the present invention.

Reference is now made to FIG. 3, which depicts a flowchart of a method to assess inflammatory changes in a mucosal tissue, according to one embodiment of the present invention. In step 300 a user may view a series of images, for example, GI tract images received for example, from an endoscope, capsule endoscope or an in vivo imaging device such as device 40. The images may be stored in a dedicated database or may be viewed in real time while being transferred, for example from an in vivo device located inside a patient's body. The user may view the images on a monitor, which may be a part of a personal computer, a workstation, PDA etc. In step 310 the series of images of the GI tract or a portion of the GI tract (e.g., the SS or colon) may be divided to several segments. For example, in some embodiments a series of images of the small bowel, may be divided to three segments, (tertiles), based on a bar such as a time bar which may be provided with an imaging device movie. According to another embodiment, images may be divided according to anatomical regions. In step 320, the user may review all the images in each segment or several selected images from each segment. According to some embodiments a parameter, for example, longitudinal extent of a lesion or size of a lesion (such as an ulcer), may be determined based on the amount of frames or images showing the lesion. In step 330, the user may select one or more images of interest or a portion of an image from the segments or from the series of images. For example, the user may select a single image from each segment and create a thumbnail of that image. Choosing and creating thumbnails may be done by operating a user interface, such as a keyboard, a joystick a mouse or any other input device. The image of interests chosen by the user may be displayed in a special display screen on the monitor. In step 340, the user may assign a mark or grade relating to several predetermined parameters, typically parameters which define mucosal damage. These parameters may be selected from database 20.

In another embodiment the user may search a specific parameter or several parameters he wishes to grade by entering one or more words of interest or keywords relating to the image of interest. The matching item may include one or more parameters highly correlated with images of interest selected. Any other search and methods may be used. The search may use local databases, for example, databases located in a workstation, a personal computer or a remote database, for example, the Internet or a dedicated health database shared with other hospitals or health organizations.

According to some embodiments of the present invention, the user may drag or otherwise translocate the images of interest or thumbnails of the images of interest into a page, e.g. a scoring page, in a reporting section of a display screen of a capsule endoscope system. In some embodiments, the page, e.g. a scoring input page, may include buttons that correspond to each of the parameters and parameter values that are to be evaluated. The user may give a mark or assign a value to each parameter per image and an algorithm or a series of medical formulas may be used to add or otherwise combine the marks up to give a final score. According to another embodiment the user selects descriptive terms that reflect the characteristics of the pathology found in a thumbnail. The software program then assigns the mark based on the descriptive terms selected.

In some embodiments, the parameters may define mucosal damage to the SB tissue. According to one embodiment the parameters may be: 1. villi appearance; 2. denuded mucosa (no villi); 3. ulcers; 4. stenosis (narrowing of the GI tract lumen). Each of these parameters can receive a mark and a final score is derived from all or some of the values given for each parameter. A final score may include a summation of all the marks. For example, a final score, of about 9 may indicate 'No Disease', a final score of 17 may indicate 'Mild disease', a final score of 33 may indicate 'No clinically significant disease, a final score of 130 may indicate 'Moderate disease' and a final score of 179 may indicate that the patient has a 'Severe disease'. The scoring can be done routinely or as a follow-up on patients at risk (e.g., patients with Crohn's disease, patients after chemotherapy, patients taking NSAIDs). The scoring can also be used to monitor mucosal healing, for example in response to treatment.

According to other embodiments a scoring index is based on three variables; villous appearance, ulcerations and stenosis. According to this embodiment analysis is carried out per tertiles created by dividing capsule transit time into three equal parts. Ulcerations can be defined, according to one embodiment, as mucosal breaks with white or yellow bases and red or pink collars. Ulcer size can be based on the entire lesion including its collar and may be measured according to the fraction of the capsule image involved by the lesion. Typically ulcer size can be based on the largest ulcer seen in each tertile.

Villous appearance can be defined, according to some embodiments, as adema where villous width is equal or greater than villous height.

According to one embodiment, a number of lesions are defined as single, few (2-7 lesions) or multiple (8 or more lesions). Small bowel segment length involvement can be defined by the percentage of a particular tertile that is involved with the mucosal change. For example, a short segment can be defined as 10% of the tertile and a long segment can be defined as 11-50% of a tertile.

According to one embodiment a stenosis score is graded on the whole sample of images being viewed, independently of individual tertiles.

According to one embodiment a final score is created by combining scores from each tertile and adding the scores for stenosis. For example, a final score may be created as follows: Adding (villous parameter×extend×descriptor)+(ulcer parameter×extend×size) for each tertile and then adding (stenosis number×ulcerated×traversed (determined by whether the capsule was able to traverse the stenosis)).

According to some embodiments the final score is based on the highest tertile score plus the stenosis score.

According to some embodiments clinically insignificant disease and mild disease are graded 0-135 whereas mild and moderate disease are graded 135-790. Sever disease is graded above 790.

Figure 4:
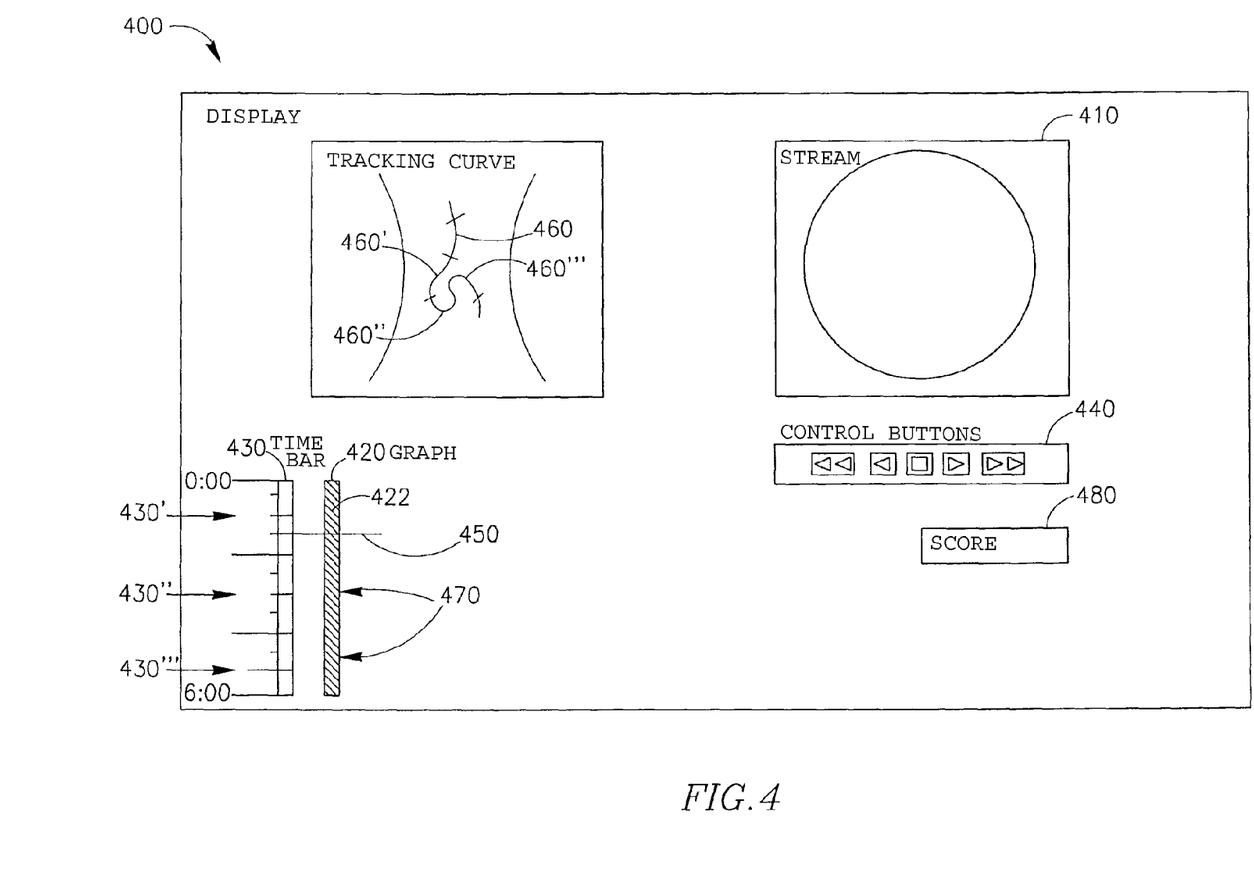
FIG. 4 shows a display of a monitor according to one embodiment of the present invention.

Reference is now made to FIG. 4 showing a display and/or a graphical user interface 400 that may be used, according to one embodiment, for preparing a report e.g. a scoring report and/or assigning a number or grade to several predetermined parameters. Display 400 may include a summarized graphical presentation 420 of an in-vivo image stream, for example, a color bar. Typically, the graphical presentation 420 may be a fixed presentation displayed alongside a streaming display of an image stream 410. In other embodiments of the present invention, graphical presentation 420 may be displayed separately. The graphical presentation 420 may include a series of colors, a series of colored areas, or a series of patterns, image items, images or pixel groups (e.g., a series of stripes 422 or areas of color arranged to form a larger bar or rectangular area), where each color in the series 422 may be associated with and/or correspond to an element or a group of elements in the original data stream. For example, each colored stripe 422 may correspond to an image or a group of images from a data stream 410. Image units other than stripes (e.g., pixels, blocks, etc.) may be used, and the image units may vary in a dimension other than color (e.g., pattern, size, width, brightness, animation, etc). One image unit (e.g., a stripe 422) may represent one or more units (e.g., image frames) in the original data stream. In one embodiment of the present invention, pointing at a stripe in a graphical presentation 20 may advance the image stream to the frames corresponding to that stripe.

In one example, a marker or indicator 450 may progress across or along the graphical presentation 420 as the substantially corresponding datum in data stream 410 (e.g., video) may be concurrently displayed to indicate the correspondence between the graphical presentation 420 and the data stream 410. According to other embodiments, the presentation may be in the form of an audio tract, graph, and other suitable graphic presentations.

An indicator 450 such as a cursor may advance along a time bar 430 and the graphical presentation 420 as the image stream 410 is scrolled on the display 400. In one example, control buttons 440 may be included in the display that may allow the user to, for example, fast-forward, rewind, stop play or reach the beginning or end of, for example, an image stream 410. In other embodiments of the present invention, a user may control the display of a data stream 410, for example, by altering the start position of the streaming display, e.g. skipping to areas of interest, by moving the position of indicator 450, for example with a mouse or other pointing device.

According to some embodiments of the present invention, the lumen being monitored e.g. the GI tract or more specifically the SB, which may be presented by tracking curve 460, may be divided into several segments e.g. tertiles 460', 460" and 460'", to enable better localization of damaged tissue or pathology. In addition, since some of the diseases associated with mucosal damage (e.g., Crohn's) can have a patchy manifestation there is a need to monitor the whole length of the lumen. There is also importance in knowing how far along the lumen the damage is. In some embodiments the lumen being monitored may be divided based on the time bar 430, e.g. time intervals 430', 430" and 430'". For example, time interval 430' may refer to tertile 460', time interval 430" may refer to tertile 460" and time interval 430'" may refer to tertile 460'". According to some embodiments, the time intervals 430', 430" and 430" are of equal size.

Make report/scoring button 480 may allow a user to initiate a scoring procedure for example as described in FIG. 2 and FIG. 3. According to some embodiments of the present invention, a user or health professional may select one or more images from the segments e.g. tertiles 460', 460" and 460'" to include in a report, e.g. scoring report. Markers 470 may be highlighted to indicate that a specific frame has been selected. Clicking or otherwise indicating 'make report/score' button 480 may advance a user to a new screen that may show, for example buttons that correspond to parameters that are to be evaluated and may provide a template for a user to prepare a report e.g. a scoring report.

In other embodiments of the present invention, a user and/or health professional may insert indications or markers such as thumbnails to mark location along the image stream for easy access to those locations in the future. For example, markers 470 may indicate from where along bar 420 candidate image frames may have been obtained.

Figure 5:
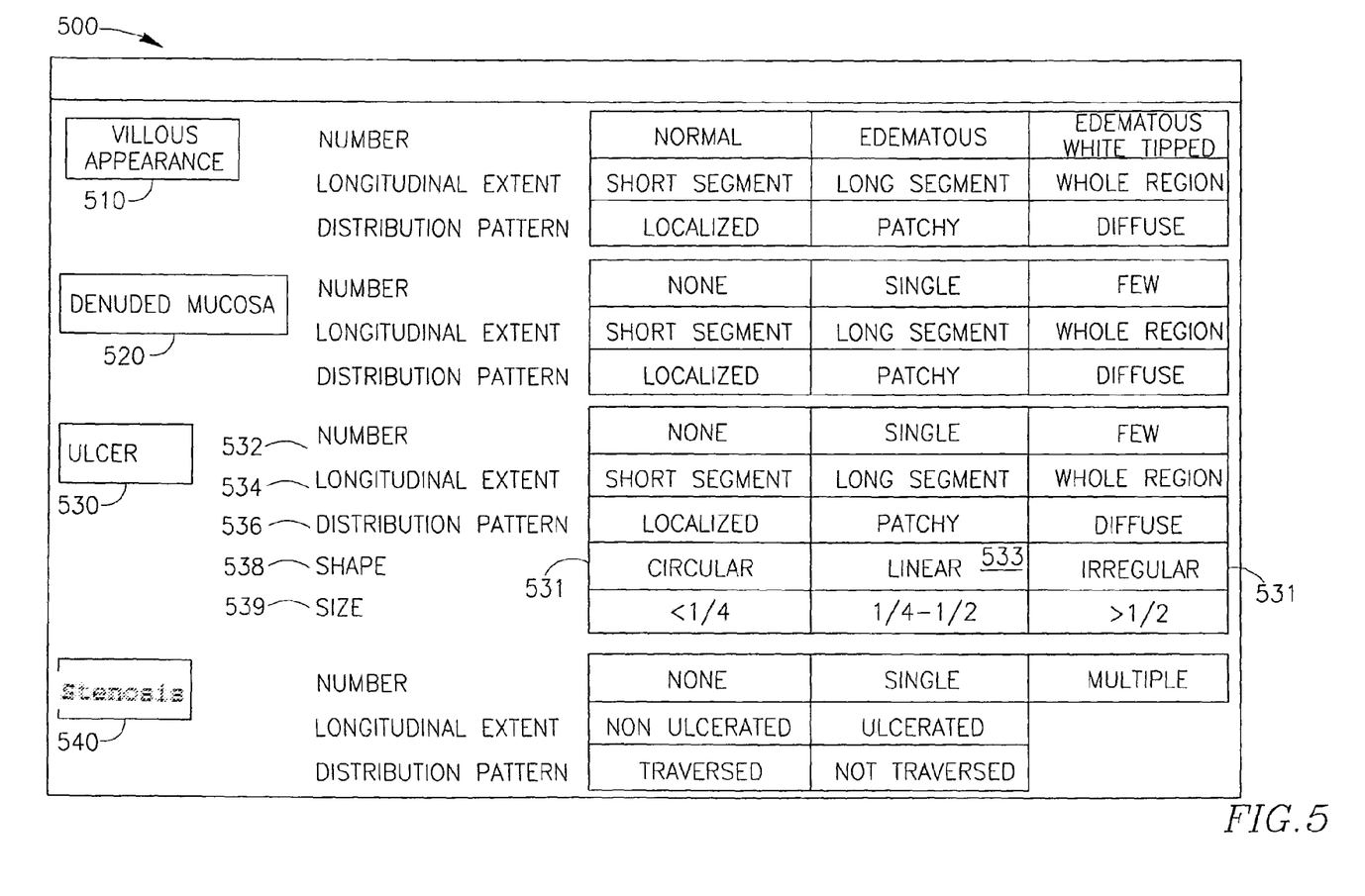
FIG. 5 shows a display of an exemplary scoring report template according to one embodiment of the present invention.

Reference is now made to FIG. 5 showing a display 500 of an exemplary scoring report template, according to some embodiments of the present invention. The display 500, may represent a scoring report template e.g. a first tertile scoring report. The display 500 may include one or more parameters, which may be derived from images of the GI tract. These parameters typically define mucosal damage to the GI tract tissue. According to one embodiment of the present invention the parameters may be villus appearance 510; denuded mucosa (no viii) 520; ulcer 530; and stenosis 540. Each parameter may include several descriptive characteristic, such as number 532, longitudinal extent 534, distribution pattern 536, shape 538 and size 539, to which the user may assign a grade. For example, a user may give a mark or grade to the shape 538 of an ulcer 530 by 'clicking' on one of the buttons 531, 533 and 535.

According to some embodiments of the present invention, the user may see a cumulative total of the score as it progresses, for example on a separate UI screen. In some embodiments, the final score may be displayed to the user after the scoring process is completed e.g. after the user finished to fill out the scoring report.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the spirit of the invention.

The invention claimed is:

1. A method, using a computing device, to assess inflammatory changes in a patient's small bowel, the method comprising:
providing to a viewer a series of images of the small bowel captured by a capsule endoscope;
dividing, using the computing device, the series of images into textiles by dividing the series of images to three groups, each group pertaining to one third of the transit time of said capsule endoscope through the small bowel;
receiving, using the computing device, scores including at least a score for at least one image from each textile, the score relating to at least one parameter defining mucosal damage;
combining the scores to obtain a final score; and
displaying the final score.

2. The method according to claim 1 wherein the parameter defining mucosal damage is selected from the group consisting of: denuded mucosa; ulceration; and stenosis and combinations thereof.

3. The method according to claim 1 wherein receiving a score comprises receiving a value for one or more factors selected from the group consisting of: number, longitudinal extent, distribution pattern, shape and size.

4. The method according to claim 1 comprising creating a thumbnail of the at least one image.

5. The method according to claim 4 comprising creating a report, said report comprising the thumbnail and the final score.

6. A system for assessing a patient's small bowel mucosa, the system comprising:
- a swallowable capsule comprising an imaging device;
- a receiver to receive images from the swallowable capsule;
- a processor to determine tertiles of the patient's small bowel, wherein each tertile comprises images of the received images captured during one third of the transit time of said swallowable capsule through the small bowel, the processor to display at least one image of each tertile; and
- the processor to accept a score for the at least one image from each of the tertiles and to calculate a final score based on the score for the images, wherein said score for the images comprises a value of a parameter defining mucosal condition, wherein the processor is to display the final score.

7. The system according to claim 6 wherein the display comprises a time bar to show a time elapsed for the at least one image of each of the tertiles.

8. The system according to claim 6 wherein the processor is to generate a report, said report comprising a combination of scores including the scores for the images.

9. The system according to claim 8 wherein the report comprises thumbnails of the images.

10. The system according to claim 6 wherein the parameter defining mucosal condition is selected from the group consisting of: denuded mucosa; ulceration; and stenosis.

11. The method according to claim 1 wherein the mucosal damage is a lesion.

12. The method according to claim 1, wherein the scores include a stenosis score based on the series of images independent of individual tertiles.

* * * * *

UNITED STATES PATENT AND TRADEMARK OFFICE
CERTIFICATE OF CORRECTION

PATENT NO.         : 8,185,185 B2                                Page 1 of 1
APPLICATION NO.    : 11/730580
DATED              : May 22, 2012
INVENTOR(S)        : Mark G. Gilreath et al.

It is certified that error appears in the above-identified patent and that said Letters Patent is hereby corrected as shown below:

In the Claims

Claim 1, Col. 10, Line 49-63 should read

1. A method, using a computing device, to assess inflammatory changes in a patient's small bowel, the method comprising:
providing to a viewer a series of images of the small bowel captured by a capsule endoscope; dividing, using the computing device, the series of images into tertiles by dividing the series of images to three groups, each group pertaining to one third of the transit time of said capsule endoscope through the small bowel;
receiving, using the computing device, scores including at least a score for at least one image from each tertile, the score relating to at least one parameter defining mucosal damage;
 combining the scores to obtain a final score; and
displaying the final score.

Signed and Sealed this
Eighteenth Day of June, 2013

Teresa Stanek Rea
*Acting Director of the United States Patent and Trademark Office*